(12) United States Patent
Bahar et al.

(10) Patent No.: US 11,273,413 B2
(45) Date of Patent: Mar. 15, 2022

(54) COMPOSITE IONOMER MEMBRANE TUBING MODULES AND SYSTEM AND METHODS INCORPORATING SAME

(71) Applicant: Xergy Inc., Harrington, DE (US)

(72) Inventors: Bamdad Bahar, Georgetown, DE (US); Harish Opadrishta, Dover, DE (US); William Parmelee, Orleans, MA (US)

(*) Notice: Subject to any disclaimer, the term of this patent is extended or adjusted under 35 U.S.C. 154(b) by 0 days.

(21) Appl. No.: 16/560,924

(22) Filed: Sep. 4, 2019

(65) Prior Publication Data

US 2020/0001238 A1 Jan. 2, 2020

Related U.S. Application Data

(63) Continuation-in-part of application No. 16/365,401, filed on Mar. 26, 2019.
(Continued)

(51) Int. Cl.
*B01D 63/06* (2006.01)
*B01D 71/36* (2006.01)
(Continued)

(52) U.S. Cl.
CPC ......... *B01D 63/063* (2013.01); *B01D 61/246* (2013.01); *B01D 61/362* (2013.01);
(Continued)

(58) Field of Classification Search
CPC .... B01D 63/063; B01D 63/043; B01D 71/36; B01D 61/246; B01D 61/362; B01D 69/10; B01D 69/12; B01D 69/04; B01D 69/02; B01D 2325/02; B01D 2325/26; B01D 2325/48; B01D 2053/223; B01D 2257/80; B01D 53/228; B01D 53/268; B01D 67/0088; C02F 1/448; C02F 2103/08; C02F 2103/023; C02F 2201/009; Y02A 20/131;
(Continued)

(56) References Cited

U.S. PATENT DOCUMENTS 3,578,175 A * 5/1971 Manjikian ............ B01D 63/065
 210/489
3,953,566 A * 4/1976 Gore ..................... B29C 55/005
 264/505
(Continued)

FOREIGN PATENT DOCUMENTS

GB 1227961 A * 4/1971 ............. B01D 71/16

OTHER PUBLICATIONS

Irvine et al. 2013. "Ion Selective Permeation Through Cellulose Acetate Membranes in Forward Osmosis".Environ. Sci. Technol. 2013, 47, 13745-13753. dx.doi.org/10.1021/es403581t (Year: 2013).*

*Primary Examiner* — Liam Royce

(57) ABSTRACT

A composite ion conducting tube is made by wrapping a support material or ion conducting sheet to from a tube having overlaps of layers that are bonded. The ion conducting sheet or tape used to make the tube may be very thin and the tube may be formed in situ by wrapping the support material and then coating with ion conducting polymer. The ion conducting tubes may be used in a pervaporation module or desalination system. The ion conducting tubes may be spirally wrapped or longitudinally wrapped and may be very thin having a tube wall thickness of no more than 25 microns.

20 Claims, 8 Drawing Sheets

Related U.S. Application Data

(60) Provisional application No. 62/765,535, filed on Sep. 4, 2018, provisional application No. 62/648,357, filed on Mar. 26, 2018.

(51) Int. Cl.
| | | |
|---|---|---|
| *B01D 61/24* | (2006.01) | |
| *B01D 69/10* | (2006.01) | |
| *B01D 69/12* | (2006.01) | |
| *C02F 1/44* | (2006.01) | |
| *B01D 61/36* | (2006.01) | |
| *B01D 63/04* | (2006.01) | |
| *C02F 103/08* | (2006.01) | |

(52) U.S. Cl.
CPC .............. *B01D 69/10* (2013.01); *B01D 69/12* (2013.01); *B01D 71/36* (2013.01); *C02F 1/448* (2013.01); *B01D 63/043* (2013.01); *B01D 2325/02* (2013.01); *B01D 2325/26* (2013.01); *C02F 2103/08* (2013.01)

(58) Field of Classification Search
CPC . Y02A 20/212; Y02W 10/37; A61M 16/0833; A61M 16/085; A61M 2230/437; A61M 2230/43; A61M 2230/432
See application file for complete search history.

(56) References Cited

U.S. PATENT DOCUMENTS 4,242,193 A * 12/1980 Moeglich ............... B01D 61/50
204/252
4,670,146 A * 6/1987 Inoue ...................... C07C 17/38
210/490
4,705,543 A * 11/1987 Kertzman ............ B01D 53/268
210/490

* cited by examiner

COMPOSITE IONOMER MEMBRANE TUBING MODULES AND SYSTEM AND METHODS INCORPORATING SAME

CROSS REFERENCE TO RELATED APPLICATIONS

This application is a continuation in part of U.S. patent application Ser. No. 16/365,401, filed on Mar. 26, 2019, entitled COMPOSITE ION CONDUCTING MEMBRANE TUBING AND PROCESS OF MAKING SAME and currently pending, which claims the benefit of priority to U.S. provisional patent application No. 62/648,357, filed on Mar. 26, 2018, and this application claims the benefit of priority to U.S. provisional patent application No. 62/765,535, filed on Sep. 4, 2018; the entirety of all of which are hereby incorporated by reference herein.

BACKGROUND OF THE INVENTION

Field of the Invention

The present invention relates to composite ionomer modules and apparatus used for drying or humidifying gases for electrochemical, medical, analytical, oil & gas applications and the like.

Background

U.S. Pat. No. 4,705,543A currently assigned to Perma-Pure LLC discloses a tubular drying device comprising of a tube which transmits water and a braided netting covering the tube; the entirety of which is incorporated by reference herein.

U.S. Pat. No. 6,779,522B2 currently assigned to Perma-Pure LLC discloses a method of manufacturing a tubular drying device used for humidification or drying of patient breathing gases in the breathing lines for patient monitoring or anesthesia results; the entirety of which is incorporated by reference herein. Said device consists of thin-walled membrane tubing which transmits water, a protective outer mesh and fittings on each end. The protective outer mesh protects the thin-walled membrane tubing from damage or from contamination by skin oils during handling.

The thin-walled membrane tubing is manufactured by inserting water permeable material into a blown film extruder. Then material is then forced through concentric extruding heads. Air is blown through the center of extruding heads to create a thin-walled tube. The thin-walled tube is then converted to the hydrogen ion form, dried and bathed in methanol to be swollen. It is then manipulated into a tubular shape.

An exemplary composite ion conducting sheet comprises a support material and an ion conducting polymer attached thereto, such as by being coated onto a surface, and/or into the pores of the support material, and/or being imbibed into the pores of the support material from one side to the opposing side. A ion conducting polymer may substantially fills the pores of the support material whereby at least 90% of the porosity of the support material is filed with the ion conducting material; as determined by a density calculation of the support material and imbibed support material. A composite ion conducting sheet or tape may be impermeable, whereby it has no bulk flow of air, wherein it has a Gurley Densometer time, according to a Gurley 4340 Automatic Gurley Densometer, Gurely Precision Instrument Inc. Troy N.Y., of more than 200 seconds.

The thin walled tube is then inserted into a protective outer mesh. The end fittings are affixed to the assembly to create the abovementioned drying device.

U.S. Pat. No. 5,980,795A currently assigned to Gkss-Forschungszentrum Geesthacht GmbH discloses a method of producing hollow fiber polymer membranes, wherein a molten polymer charged with a gas under pressure is extruded the entirety of which is incorporated by reference herein.

The extrusion process used to manufacture PFSA (Perfluorosulfonic acid) tubes is essentially a twostep process. The extrusion process uses melt processable polymers and then goes through a post sulfonation step. The melt processable polymers that are used must be inherently strong i.e. relatively low acidity due to high equivalent weight.

U.S. Pat. No. 8,366,811B2, U.S. Pat. No. 9,067,035B2, U.S. Pat. No. 8,747,752B2 currently assigned to Oridion Medical (1987) Ltd. disclose dryer polymer substances adapted to pervaporate a fluid (such as water, water vapor or both) and their methods of preparation. U.S. Pat. No. 8,747,752B2 discuss a dryer polymer substance that included: a porous support member and a cross-linked co-polymer comprising a) a cationic monomer and an anionic monomer, b) a zwitterionic monomer, or a combination thereof; the entirety of which is incorporated by reference herein.

The entirety of all patents and applications in the background are hereby incorporated by reference herein.

SUMMARY OF THE INVENTION

The invention is related to pervaporation modules comprising very thin ion conducting sheets of material generally referred to as ion conducting membrane. The ion conducting tubes are from ion conducting polymers and preferably thin composite ion conducting membranes comprising an ion conducting polymer and a support material. In an exemplary embodiment, a support material is a porous membrane, such as a porous fluoropolymer membrane, supports an ion conducting polymer to enable the composite to be very thin, such as less than 50 µm, and preferably less than 25 µm and even more preferably less than 15 µm, and even more preferably less than 10 µm. A thin composite ion conducting membrane may be made into a pervaporation tube by wrapping, either spirally or "cigarette wrap. In an exemplary embodiment, the ion conducting sheet or tape is wrapped around a mandrel to form the ion conducting tube. Note that an ion conducting sheet or tape may be wrapped any number of times, such as two or more times to produce a plurality of layers of the support material through the tube wall. An exemplary ion conducting sheet is double helically wrapped, such as around a mandrel, to form the ion conducting tube.

The wrapped composite ion conducting membrane may have bonded areas wherein at least a portion of the overlap area is bonded together, such as by being fused, or laminated, or thermally welded together, or wherein the ion conducting polymer from one layer is bonded with an ion conducting polymer layer of a second layer or with a support material of a second layer. These bonded areas may be thicker than non-bonded areas where a single layer of the ion conducting. The overlapped width of a bonded area may be fraction of the tape width, such as no more than about 30% of the tape width, no more than about 25% of the tape width, no more than about 20% of the tape width, no more than about 10% of the tape width, or even no more than about 5% of the tape width to provide a high percentage of the spiral wrapped tube 32 that is only a single layer, thereby increase the rate of transfer of ions through the tube. The bonded areas may make up some proportion of the ion conducting tube surface area, wherein the surface area is the product of the outer circumference of the tube and the length of the tube. The bonded areas may be a proportion of the tube surface area, such as no more than about 30%, no more than about 25%, no more than about 20%, no more than about 10%, or even no more than about 5%, or any range between and including the percentages provided. A low percentage bonded area may provide a higher percentage of thin ion conducting tubing and improve ion transfer and effectiveness of the system. A longitudinally wrapped tube may have a very low percentage of bonded area, as the bonded area may extend along the length and not around the tube as is the case with a spiral wrapped tube. A spiral wrapped tube may however be stronger and less prone to breaking under pressure.

According to one embodiment of the present invention, there is provided a tubular structure comprising of a porous support layer and an anionic or a cationic polymer. The tubular structures have overlapping "bonded areas".

According to one embodiment of the present invention, the porous support layer is further reinforced with mandrel used to provide strength and rigidity. An exemplary mandrel may extend within the tube conduit or the ion conducting tube may configured within the mandrel. The mandrel may resist expansion or contraction of the ion conducting tube due to pressure difference between the outside and inside surface of the tube. An exemplary mandrel is permeable and may have apertures through the mandrel wall to enable fluid contact on both the outside and inside surfaces of the ion conducting tube.

According to one embodiment of the present invention, there is provided a process for the preparation of the membrane tubes by tape-wrapping a porous support material, such as a porous polymeric material, around a mandrel. The mandrel may then be heated, such as by being passed through a heating chamber or an infrared chamber, to fuse the wrapped support material into a continuous tubular structure. The tubular structure may then be passed through a coating process wherein the porous tube is coated with the ion conducting polymer. The assembly may then be dried, such as by being air dried or by being passed through a dryer to dry the porous tubes after the coating process. A dryer may be a radiant dryer or a forced air dryer, for example. The dried ion conducting tube may then be dipped in water and swollen, when the ion conducting polymer is hydrophilic and swell with water. The tubes may then be removed from the mandrel and dried once again back to approximately an original size. In some cases, the ion conducting tube may be left on the mandrel and the mandrel may provide support for pressure difference in use. The mandrel may also enable potting of the ion conducting tube in a module.

According to one embodiment of the present invention, a support material is wrapped around a mandrel and then coated with ion conducting material and then dried to produce a composite ion conducting tube on a mandrel. The composite ion conducting tube may be removed from the mandrel or may be used with the mandrel as a support mandrel in an application.

According to one embodiment of the present invention, a composite ion conducting sheet is wrapped around a mandrel and then bonded together, wherein the overlap areas are bonded together to form bonded areas and to form the tube. The composite ion conducting tube may be removed from the mandrel or may be used with the mandrel as a support mandrel in an application.

According to one embodiment of the present invention, a composite ion conducting sheet is wrapped around a mandrel while the ion conducting polymer is dissolved in a solvent. The wrapped mandrel may then be dried to bond the overlap areas of the wrapped support layer together. The solution of ion conducting polymer and solvent may imbibe the support material and form an air impermeable layer to form the ion conducting tube. Again, the composite ion conducting tube may be removed from the mandrel or may be used with the mandrel as a support mandrel in an application.

According to one embodiments of the present invention, there is provided a process for the preparation of tubular structure adapted to pervaporate the fluid by helically wrapping one or more membranes around a cylindrical structure and using heat or infrared radiation on the assembly to fuse the wrapped membrane tapes into a continuous cylindrical structure.

According to one embodiment of the invention, we describe a method to put structural meshes around the tubes for structural rigidity. This is accomplished by passing the structural mesh over the tube and using adhesive lined heat shrink at the ends to bond the structural mesh to the ionic tube.

According to one embodiment of the invention, a method for putting fittings at the ends of the tubes is described. A rigid plastic tubing may be inserted at the ends of the ionic tubing, and insert the plastic tubing into different kinds of fittings such as compression, barbed, push-to-connect, etc. Adhesive lined heat shrink may be used to attach the ionic tubing to rigid plastic tubing.

The manufacturing processes described above ensure that the tubes are much thinner than those described in the prior art. The thinness of the tubes along with the greater ionic nature of the material ensures tubes which permeate water, water vapor with greater ability.

According to one embodiments of the present invention, there are provided devices, modules, which employ pervaporative tubing to dry incoming air streams for medical, analytical, electrochemical and oil and gas purposes. Several pervaporative tubes are forced into a cylindrical structure which constitutes the shell. The pervaporative tubes are capped off and then dipped into potting resin. Once, the potting resin and seals all tubes in place, the process is repeated on the other end of the tubes. Finally, the ends are capped off with front and rear headers.

The modules provide a number of key features and benefits including: Ultra-thin composites are usable to make these tubes. The tubes that are very strong, and therefore can handle a high pressure feed. Because of the combination of strength and the thin nature of the ion conducting tube, there is less resistance to permeation which enables higher performance tubular systems. Because of the ultra-thin structure, less expensive ion conducting polymer material is used to produce these tubes, therefore the units have inherently lower cost, and therefore the technology can be applied to wider range of applications beyond the current thick walled, extruded tubes that are present in the market.

The technology is ideally suited for desalination, ionic liquid desiccation, waste processing and numerous other applications. A membrane-based desalination unit utilizing the ion conducting tubes described herein may be a stand-alone unit which fits in a 3.048 m (10 ft) shipping container.

This technology can provide a compact, portable seawater desalination system utilizing solar energy. This is a derivative product leveraging Xergy's current program to supply the Department of Energy/U.S. Navy with a 100 gallon per day Solar Vacuum Desalination System (VD) based on its "Advanced Composite Polymer Electrolyte membranes (PEM)" which will be installed at San Clemente Island (California) under DOE funding.

The core technology behind the desalination unit is explained in FIG. 1. At the heart of this technology is the heat exchanger module which exchanges heat between the incoming cold membrane circulating stream and the steam obtained from the membrane contactor.

This enables us to simultaneously condense steam as well as heat the incoming sea water feed. The membrane contactor unit is comprised of ion exchange membranes and purifies water by pervaporation to salinity levels below 60 ppm as shown in Table 1. From Table 1, the moisture flux is highly dependent on the brine temperature at a fixed vacuum.

TABLE 1

Respective yield for each temperature, flux rate, final salinity and change in salinity.

| Trial # | Water temp (C) | Duration (min) | Mass (g) | Flux rate (g/hr · m^2) | Salinity in (%) | Salinity out (%) | Salinity difference (%) |
|---|---|---|---|---|---|---|---|
| 1 | 40 | 45 | 2.51 | 259.43 | 2.6 | 0.0033 | 99.873 |
| 2 | 58 | 45 | 23.965 | 2477.00 | 2.5 | 0.006 | 99.764 |

The pervaporation modules and pervaporation tubes comprising an ion conductive polymer and preferably a composite ion conductive membrane that is thin may be used in any of the following application, U.S. provisional patent application No. 62/244,709, filed on Oct. 20, 2015, U.S. provisional patent application No. 62/385,178 filed on Sep. 8, 2016, U.S. patent application Ser. No. 15/698,886 filed on Sep. 8, 2016, and U.S. provisional patent application No. 62/594,091, filed on Dec. 4, 2017; the entirety of each patent application is incorporated by reference herein. An exemplary ion conducting polymer in an ionomer, or proton conducting polymer, such as sulfonated tetrafluoroethylene based fluoropolymer-copolymer, as perfluorosulfonic acid.

An exemplary pervaporation tube comprises a composite ion conducting sheet, or membrane, as described in any of the embodiments herein. An exemplary pervaporation tube may be spirally wrapped or longitudinally wrapped with the composite ion conducting sheet. An exemplary pervaporation tube may be configured in a module to exchange moisture form within the tube conduit of the ion conducting tube to outside of the ion conducting tube or vice versa. A module, such as a pervaporation module may have any number of ion conducting tubes therein, such as two or more, five or more, ten or more, twenty or more and any range between and including the numbers provided. The diameter of the ion conducting tube may be small to increase the surface area exposed, such as no more than about 50 mm, no more than about 25 mm, no more than about 10 mm, no more than about 5 mm, no more than about 3 mm and any range between and including the values provided. An exemplary module comprising an ion conducting tube as described herein may be a desalination module.

The membranes may be made with polymer materials which include but are not limited to Perfluorosulfonic acid (PFSA), Polyether block amide (PEBA), Polyurethane (PU) or blends of the mentioned polymers.

One application for the membrane modules is desalination where the hollow fiber membranes are used as separator materials. A 3D model of the membrane module is show in FIG. 9. An exploded view of desalination module is provided in FIG. 10. The separator material may be any material that allows water vapor to pass therethrough but prevents liquid water from passing and may be a hydrophobic membrane, or a thin film of material including, but not limited to, an ionomer, a urethane or other polymer having a high moisture vapor transmission rate, MVTR. Other separator materials included, but are not limited to, Nation®, PSFA, PEBA, sulfonated PEEK (poly ether ether Ketone), PES (poly ether sulfone), Polymer-SEBS, poly (arylene), and polyolefin, sulfonated urethanes. A separator membrane may be non-air permeable, having no bulk flow of air therethrough, and may be film. A non-air permeable separator, as used herein will have a Gurley value of about 100 seconds or more, and preferably 200 second or more, and in some cases about 500 seconds or more, as measured by an Automatic Gurley Densometer, 4340, from Gurley Instruments Inc.

An exemplary separator material may be very thin to increase the MVTR , or rate of transfer of the water vapor and may have a thickness of about 50 micron or less , about 25 microns or less , about 15 microns or less and any range between and including the thickness values provided. A separator material may comprise a support material that mechanically reinforces the separator material such as a net, mesh, woven material or membrane. An exemplary support material is an expanded polymer membrane and water vapor polymer, such as an ionomer or urethane may be imbibed into or otherwise attached to the expanded membrane. An exemplary expanded polymer membrane is expanded poly tetrafluoroethylene, available from W. L. Gore and Associates, Inc. An expanded polymer membrane may be preferred as it is very thin and strong.

An additional use for modules is dewatering of organic solutions. Some examples of organic solutions are but not limited to solvents, fragrances, juices, syrups, lubricants, fuel and oils.

Membrane modules are also used in HVAC applications. A major application for the modules includes liquid desiccant dehumidification, where, the process or feed air is dehumidified by a liquid desiccant and dried. The liquid desiccant picks up moisture from the air and gets diluted. It is then concentrated in another desiccant module using exhaust air ducted from the condenser. The hollow fiber membranes being used should be compatible with the liquid desiccant at operating temperatures.

Exemplary modules are made leak proof by designing the tube sheets to contain two potting resin channels, The holes drilled in the tube sheet are sized to provide a friction fit when the membrane tubes terminated with hard tubing are inserted into them. The resin channel on the inside of the tube sheet is appropriately sized to the right depth—to ensure that the potting resin envelopes the joint between the heat shrink, membrane tubing and hard tubing. The two resin channels are filled with potting resin and the potting resin is cured. We add structural support elements to the prevent the module from buckling.

Another HVAC application for the membrane modules employing hollow fiber membranes is an energy recovery ventilator. An energy recovery ventilator is used to contact the ventilation air with exhaust air, thus recovering energy from the exhaust. The membrane modules consisting of hollow fiber membranes would essentially work as a shell and tube membrane contactor and contact ventilation air flowing in the tube side with exhaust air flowing in shell side or vice versa.

The modules containing the ionic membrane tubes can also be used to provide cooling in an evaporative cooling setup. In this application, water is flown through the inside of the tubes and fan blows air across the module. The water inside the tubes gets cooled down to the dew point temperature by the principle of evaporative cooling—water vaporizes and permeates through the semi permeable membrane and gets transported away from the membrane by the draft from the fan.

A medical gas-conditioning application for membrane modules employing hollow fiber membranes is drying/humidification of medical gases in but not limited to sampling lines, anesthesia monitoring, capnography. An image of a sample medical gas dryer/humidifier is shown in FIG. 13. The medical gas flows inside the membrane tube and dried with the help of a gentle vacuum or purge gas.

Another configuration of operation for the medical gas-conditioning membrane module is running the medical gas on the shell side and drying it with a vacuum or a purge gas in the tube side.

The membrane tubes used for the gas-conditioning application may be terminated at the ends with hard tubing the same size as membrane tubing. The hard tubing is inserted into the hollow fiber membrane and sealed with the help of heat shrink tubing.

The membrane, hard tubing assemblies are then terminated with the help of fittings of different kinds such as but not limited to push-to-connect, compression and luer fittings.

In fuel cells, membrane modules are used to humidify/dehumidify the hydrogen and oxygen/air streams that are used in fuel cells. An image of a sample fuel cell dehumidifier/humidifier is shown in FIG. 14.

The membrane modules containing hollow fiber membranes are used in analytical gas conditioning applications. The modules are used to dry or humidify gases in but not limited to marine gas sampling, diesel emissions monitoring, mercury analyzers, NOx analyzers, and $CO_2$ analyzers.

An exemplary ion conducting polymer membrane module may be used in a wide variety of applications and systems and may provide hydration, dehydration of gas with little contamination. Some system require very clean gas with very low levels of contamination or impurities, such as analytical gas conditioning systems and medical gas conditioning.

Evaporative Cooling: In an HVAC system, heat is generated by the sun shining on the building, the computers, and people. The heat is picked up in the air handlers which are indirectly tied to the refrigerant through several heat exchangers. The heat boils the refrigerant from a liquid to a vapor. In order to convert this vapor back to a liquid, we use cooling tower water. The refrigerant vapor is condensed, and heat is transferred to the water with the help of a heat exchanger. The purpose of the cooling towers is to cool the warm water returning from the heat exchanger. The cooling towers consist of a plurality of ionic membrane tubes through which the warm water flows. Some of the warm water vaporizes, and the vapor transfers through the ionic membranes. A fan providing a draft drives the water vapor away from the cooling tower. This process cools the warm water down by removal of latent heat of vaporization. The cooled water is then looped back to the heat exchanger to condense the refrigerant vapor. These membrane modules provide an advantage over conventional cooling towers as they provide closed circuit evaporative cooling. This prevents microbial growth which is common to open circuit systems and hence a much more Analytical gas conditioning: Gas drying lines can also be used to dry gases prior to analysis or generating dry air for mercury analyzers, CO2 analyzers and NOx analyzers. We can sample highly reactive corrosive gases due to the use of inert fluoropolymers. We have no analyte losses due to the use of dense membranes and wrapping more than one layer of membrane to prevent tiny leakages at the crease.

Hydrogen gas dryers: Electrolyzers generate hydrogen by electrolytically splitting water. The hydrogen generated by this process is wet (mixed with water vapor). Hydrogen gas dryers remove water vapor from hydrogen before bottling.

Fuel cell humidifiers: Hydrogen flowing into the fuel cell needs to be humidified in order to achieve optimum performance of fuel cell. Gas humidifiers may be tube-in-shell humidity exchangers that transfer heat and water vapor between two gas streams, process and feed fluids. They may operate as either water-to-gas or gas-to-gas humidity exchangers. Water-to-gas humidifiers have liquid water on one side of the tube wall and a dry gas on the other. This arrangement offers the greatest amount of humidification; however, the reaction of the water molecules moving through the tubing wall absorbs heat. To counter this cooling effect, the inlet water must be heated. Hot, circulated deionized water should be used to optimize performance. Gas-to-gas humidifiers use counter-flowing wet and dry gas streams to move heat and humidity from one stream to the other. These units are energy efficient, as they do not require any additional power or heat. When gas passes inside the ionic tubing, water is absorbed by and moves through the walls of the tubing. The movement of water is driven by the humidity gradient between the inside and outside of the tubing. Since only water molecules move through the tubing walls, liquid water is prevented from becoming entrained in the gas stream.

Medical gas conditioning: Water vapor needs to be removed from breath samples for accurate breath gas analysis. The most common source of problems in breath gas analysis is the water vapor present in the sample. It can cause condensation in gas sampling lines and measurement cells as well as interference with (IR) $CO_2$ monitoring. Exemplary humidity exchangers selectively remove only water vapor from the sample, virtually eliminating this source of analyzer failure. The gas flows through the ionic membrane tube and is dried out by using purge gas or applying vacuum on the shell side or vice-versa. Humidity Exchangers are widely used for Anesthesia monitoring, Stress testing/Pulmonary function testing, Capnography (CO2 monitoring) and Asthma monitoring (Nitric Oxide).

Desert Coolers: These are air coolers which work on the principles of evaporative cooling. A module with exposed ion conducting tubes may be used in a desert cooler system when coupled with a fan and a fill.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
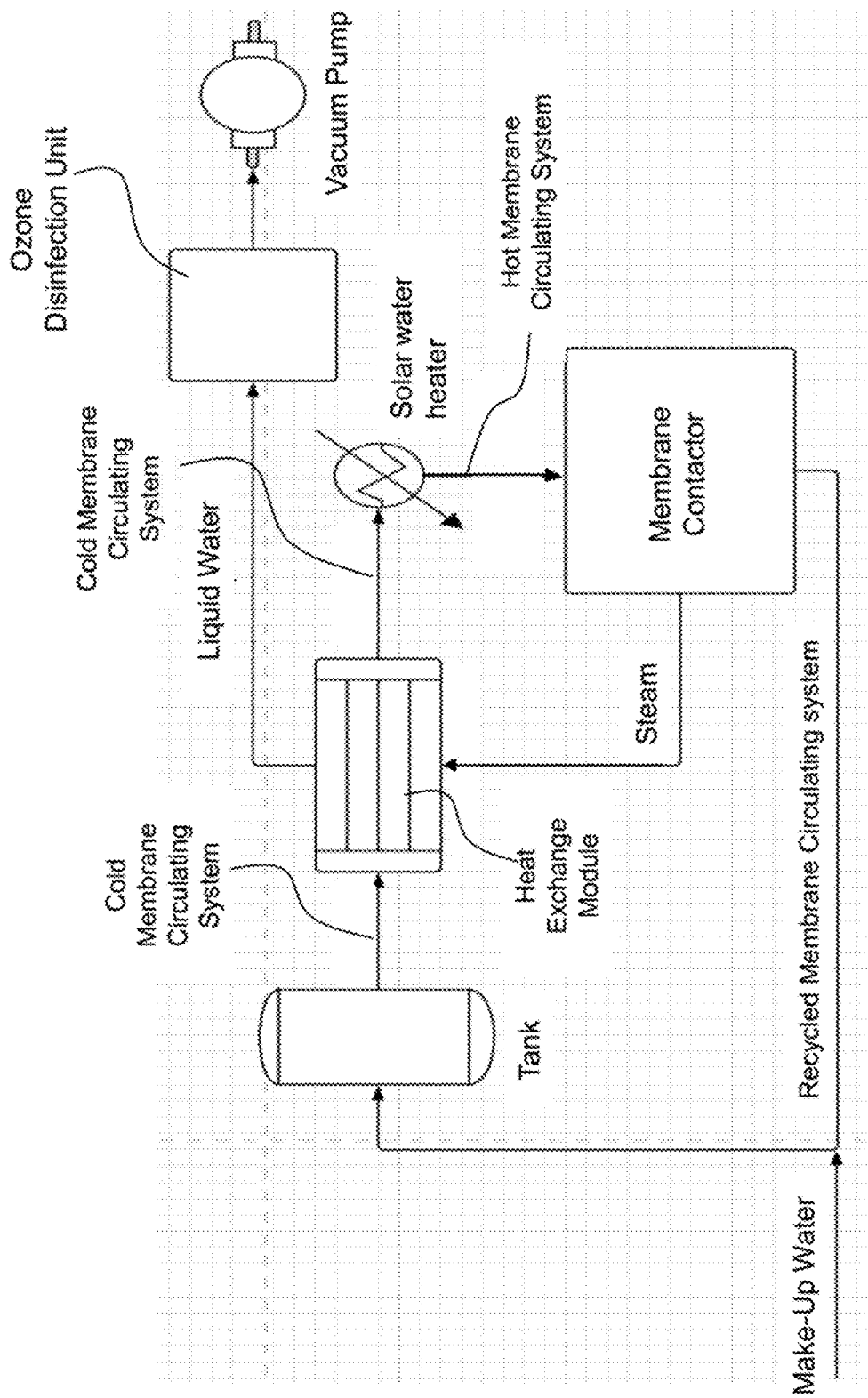
FIG. 1 is a diagram of a pervaporation unit.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary heat exchanger module which exchanges heat between the incoming cold membrane circulating stream and the steam obtained from the membrane contactor.

Figure 2:
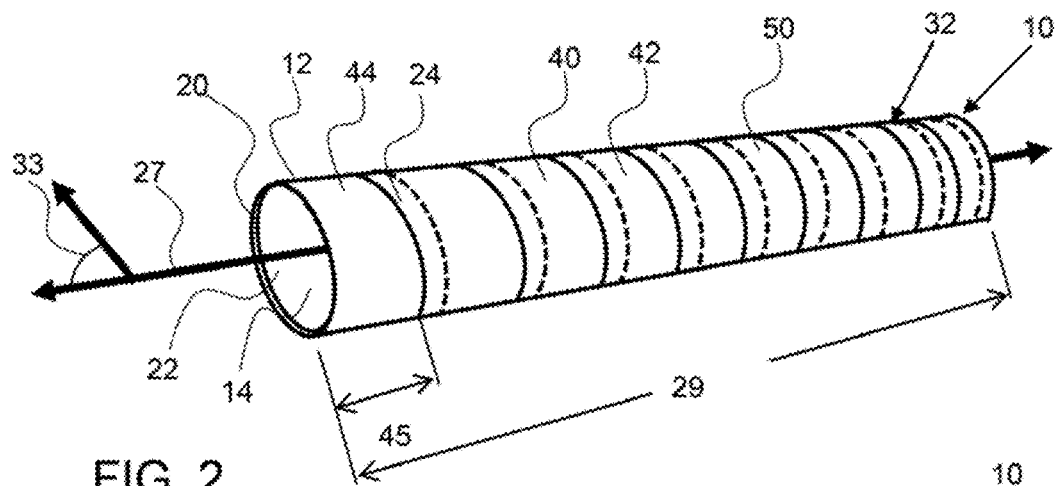
FIG. 2 shows a perspective view of an exemplary ion conducting tube comprising a spirally wrapped ion conducting membrane sheet to form a spiral wrapped ion conducting tube.
Figure 7:
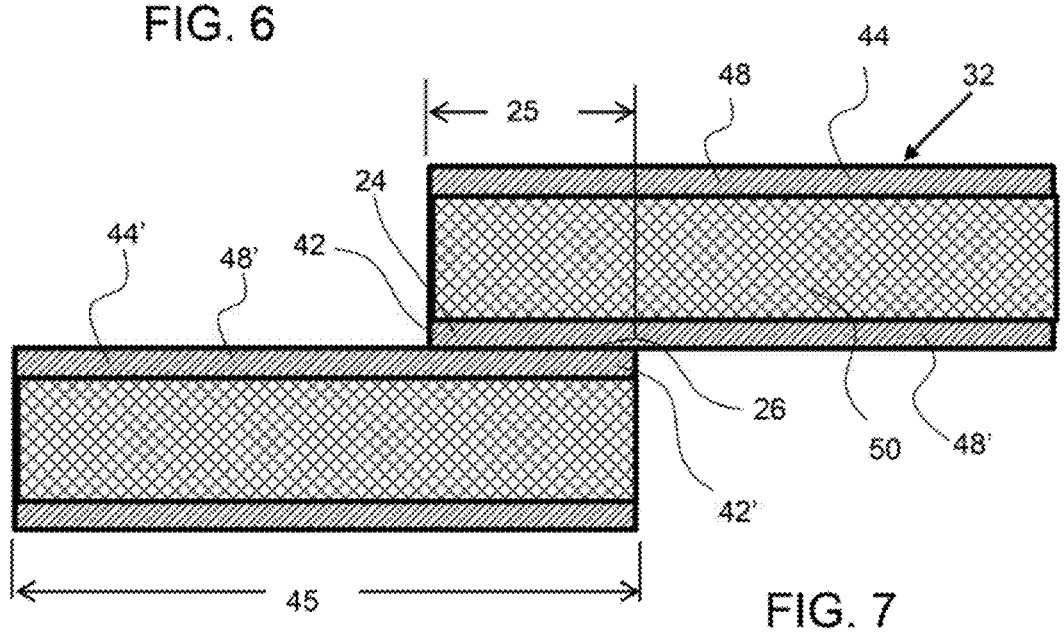
FIG. 7 shows a cross sectional view of an exemplary spiral wrapped tube comprising ion conducting tape that is bonded together in an overlap area.

Referring to FIGS. 2 and 7, an exemplary ion conducting tube 10 comprises a spirally wrapped ion conducting membrane sheet 40, or ion conducting tape 44 to form a spiral wrapped ion conducting tube 32. The ion conducting tube 10 is has a tube wall 20 formed by the spirally wrapped ion conducting tape 44 that is wrapped at a wrap angle 33 with respect to the longitudinal axis 27 of the tube, or length axis of the tube, a line extending along the center of the tube conduit 22. An exemplary wrap angle may be 80 degrees or less, 75 degrees or less, 60 degrees or less, 45 degrees or less, 30 degrees or less and any range between and including the wrap angles provided. A smaller wrap angle may provide less overlap area and therefore better performance. The tube has an outside surface 12 and an inside surface 14, and a tube conduit 22 extending along the length 29 of the tube. The ion conducting tape 44 comprises an ion conducting polymer 42 and a support material 50, and has a width 45. The spiral wrap forms an overlap area 24 between adjacent tape wraps and this overlap area has an overlap with 25 as shown in FIG. 7. As shown in FIG. 7, the ion conducting polymer 42 of a first layer of the ion conducting tape 44 is bonded to the ion conducting polymer 42' of a second layer of the ion conducting tape 44' to form the bonded area 26. As described herein the overlap width may be fraction of the tape width, such as no more than about 30% of the tape width, no more than about 25% of the tape width, no more than about 20% of the tape width, no more than about 10% of the tape width, or even no more than about 5% of the tape width to provide a high percentage of the spiral wrapped tube 32 that is only a single layer, thereby increase the rate of transfer of ions through the tube. The tube wall thickness 21 is the thickness of the bonded area or both layers in the overlap area and the tube wall thickness is the thickness of a single ion conducting tape 44 otherwise.

Figure 3:
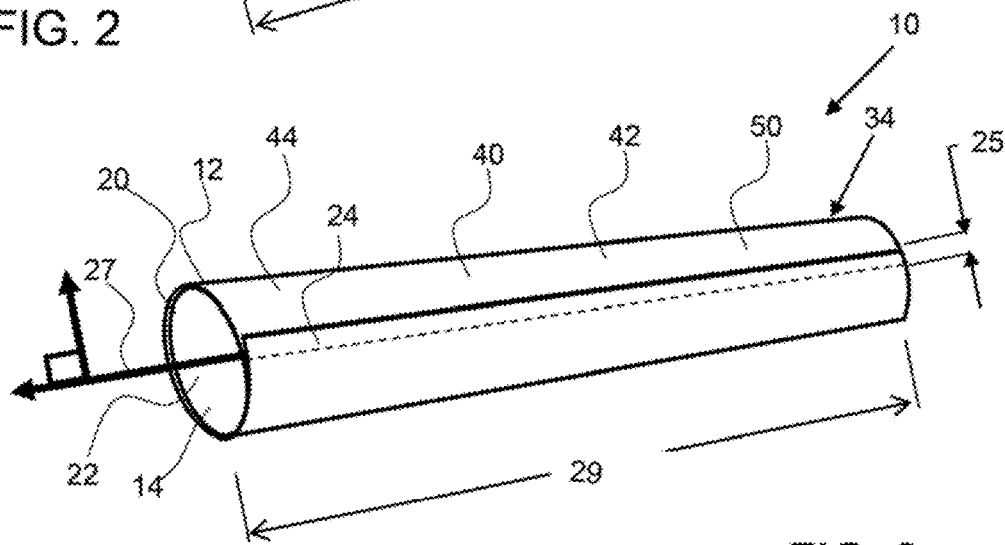
FIG. 3 shows a perspective view of an exemplary ion conducting tube comprising a longitudinally wrapped, or "cigarette wrapped" ion conducting membrane sheet to form a longitudinally wrapped ion conducting tube.

As shown in FIG. 3, an exemplary ion conducting tube 10 comprises a longitudinally wrapped, or "cigarette wrapped" ion conducting membrane sheet 40 to form a longitudinal wrapped ion conducting tube 34. The ion conducting sheet 40 is wrapped around the longitudinal axis 27 of the tube. In this embodiment, the length of the tube 29 is the width of the ion conducting sheet and the wrap angle is perpendicular to the longitudinal axis 27. The longitudinal wrapped ion conducting tube 34 has an overlap are 25 having an overlap width 25. Again, the overlap width may be no more than about 30% of the tape width, no more than about 25% of the tape width, no more than about 20% of the tape width, no more than about 10% of the tape width, or even no more than about 5% of the tape width to provide a high percentage of the spiral wrapped tube 32 that is only a single layer, thereby increase the rate of transfer of ions through the tube.

Figure 4:
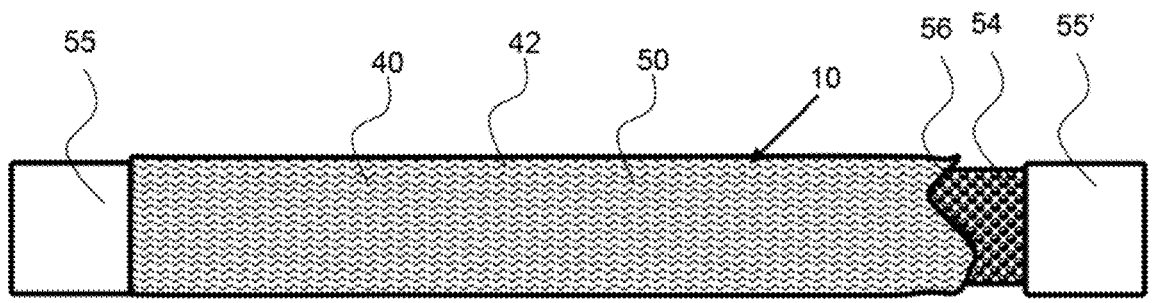
FIG. 4 shows a side view of an ion conducting tube configured over a support mandrel having apertures to allow fluid contact with the ion conducting tube.

As shown in FIG. 4, an ion conducting tube 10 is configured over a support mandrel 54 having apertures 56 to allow fluid contact with the ion conducting tube. A support mandrel may be rigid, such as a metal or plastic tube, or may be pliable and able to bend and flex. The apertures may form a substantial part of the mandrel and may be at least 50% of the area, at least 75% of the area, at least 80% of the area, at least 90% of the area, whereby the higher the aperture area percentage the higher the contact of fluid with the ion conducting tube, and therefore more ion transfer. The exemplary mandrel has adapter ends 55, 55' that may comprise a fitting for attachment to a module frame.

Figure 5:
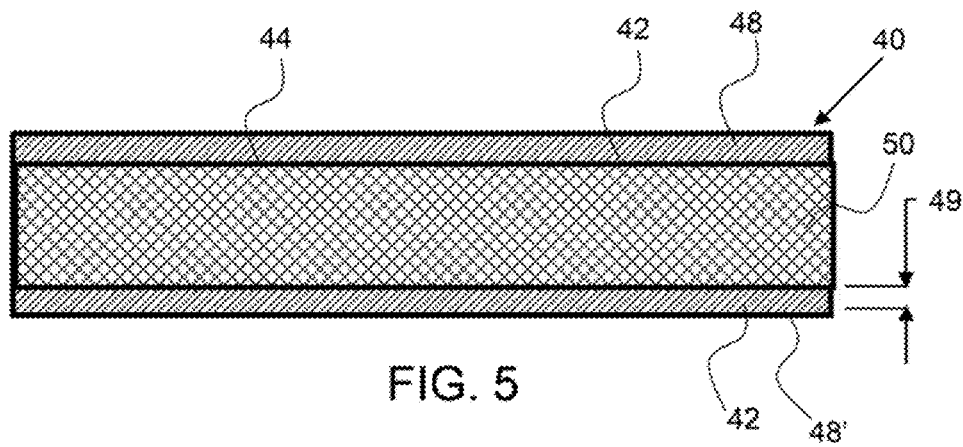
FIG. 5 shows a cross sectional view of an exemplary ion conducting sheet comprising an ion conducting polymer and a support material.
Figure 6:
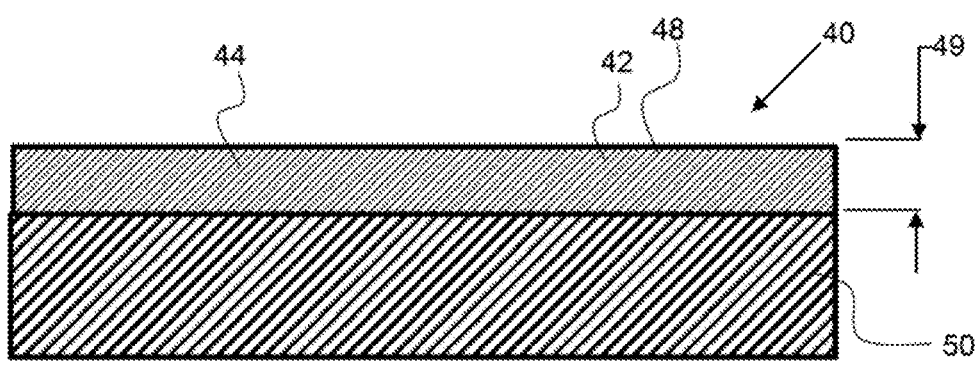
FIG. 6 shows a cross sectional view of an exemplary ion conducting sheet comprising an ion conducting polymer and a support material.

Referring now to FIGS. 5 and 6, an exemplary ion conducting sheet 40, such as an ion conducting tape 44, comprises an ion conducting polymer 42 and a support material 50 and has a single sheet thickness 41. A tape is simple a sheet that is narrow and conducive for spiral wrapping. The support material may be a porous material and the ion conducting polymer, such as an ionomer, may fill a substantial portion of the pores in the support material, such as by being imbibed into the support material. The ion conducting polymer may extends along one or both of the opposing surfaces of the composite ion conducting sheet as a surface layer 48 and has a surface layer thickness 49. In FIG. 5, the ion conducting polymer fills the pores of the support material and extends along both opposing surfaces. As shown in FIG. 6 the ion conducting polymer is imbibed into the support material and extends along one surface of the support material.

As shown in FIG. 7, the ion conducting layers extending along the opposing surfaces are bonded together in the overlap area 24 to form a bonded area 26 between the surface layer 48' and surface layer 48. Note that the surface layer may extend into the support 50 to bond layers of ion conducting sheets or tapes together. A fluid tight seal may be formed by the overlap and bonded area.

Figure 8:
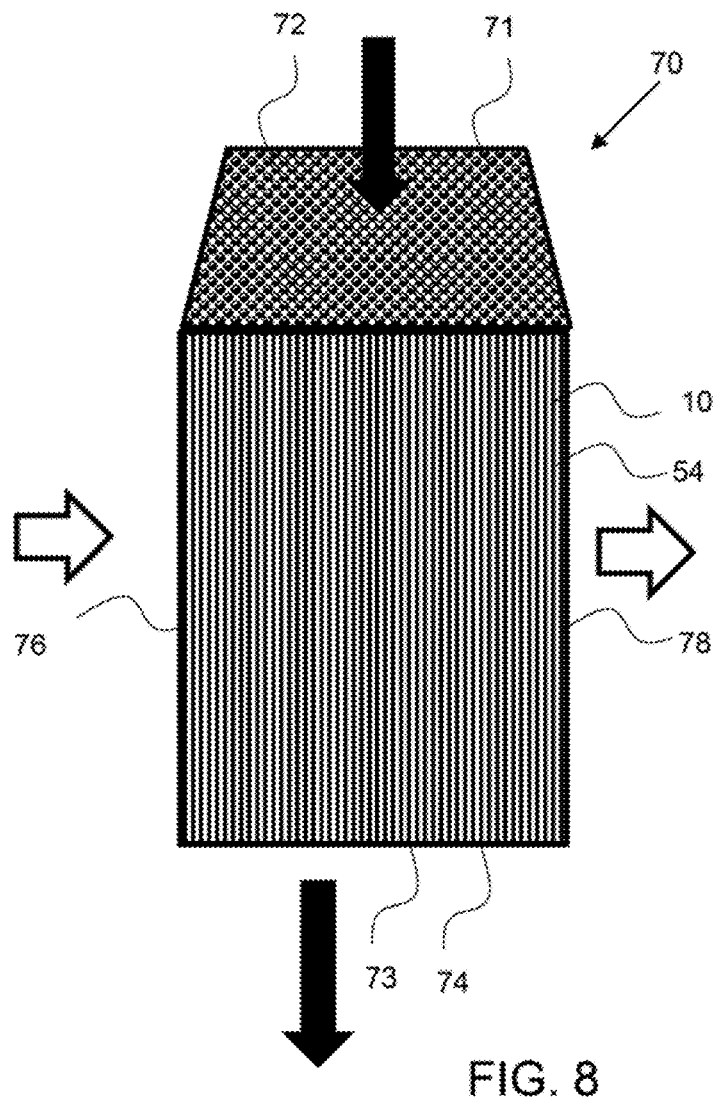
FIG. 8 shows an exemplary module comprising a plurality of ion conducting tubes, as described herein.

As shown in FIG. 8, an exemplary ion conducting polymer module 70 comprises a plurality of ion conducting tubes 10 that extend from a tube inlet 72 to a tube outlet 74. A flow of fluid flows through the tubes and a cross flow of fluid flow around the outside surface of the tubes from a cross-flow inlet 76 to a cross-flow outlet 78. Moisture may be transferred from or to the cross-flow fluid depending on the desired arrangement. The ion conducting tubes may be potted with potting 75 or otherwise attached to the inlet frame 71 and outlet from 73. Each tube may be configured around a mandrel 54 and the mandrel may have ends that are conducive to potting or attachment to the frame. The mandrel may have an adapter end 55 which comprises a fitting on the ends that can be secured to the frame and the adapter may have threads or beveled ends for sealing. Also note that the mandrel may have apertures along the center portion but not proximal the ends where the mandrel is attached to the frame.

Figure 9:
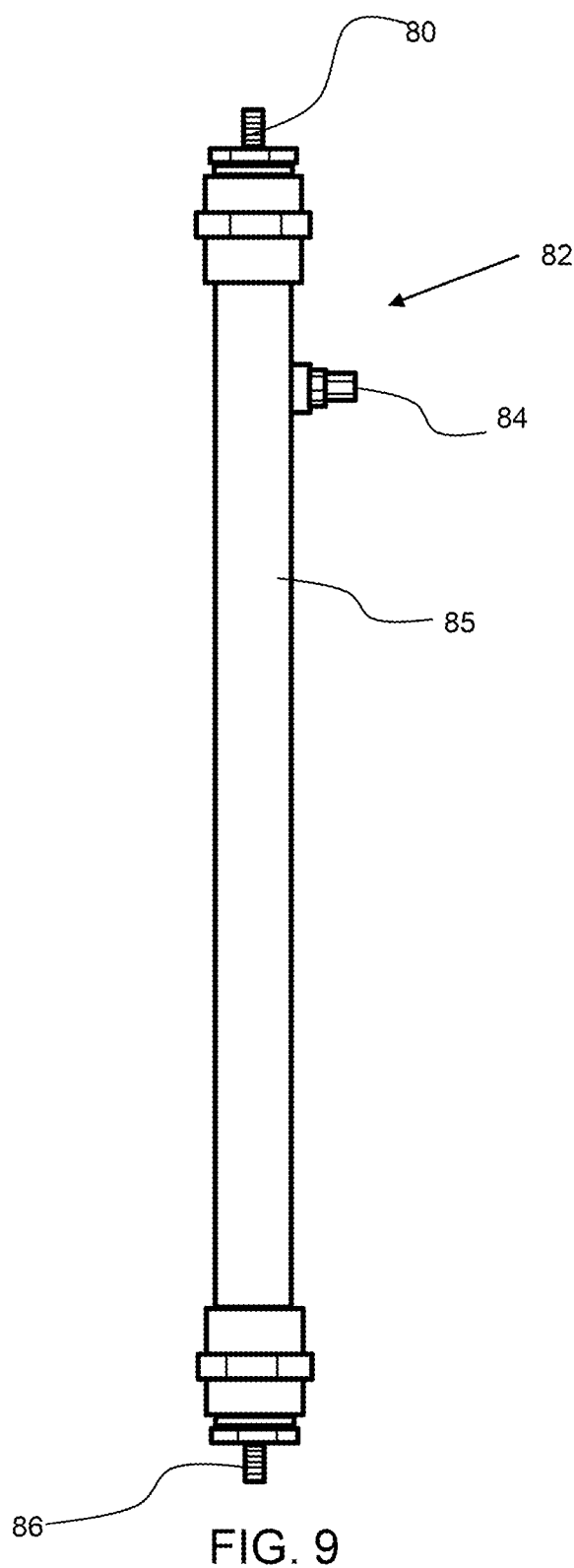
FIG. 9 shows a side view of an exemplary shell and tube assembly comprising a helical membrane structures.

As shown in FIG. 9, an exemplary module 82 used for desalination, wastewater treatment and removal of water from organics is displayed. The organic solution or wastewater flows into a plurality of ion conducting tube inside the module enclosure 85, a tube in this embodiment. The wastewater flows through through the inlet 80 and flows out through the outlet 86. The liquid inside the tubes is subjected to a gentle vacuum between the module enclosure 85 and ion conducting tubes. A vacuum may be drawn by a pump connected to the vacuum port 84.

Figure 10:
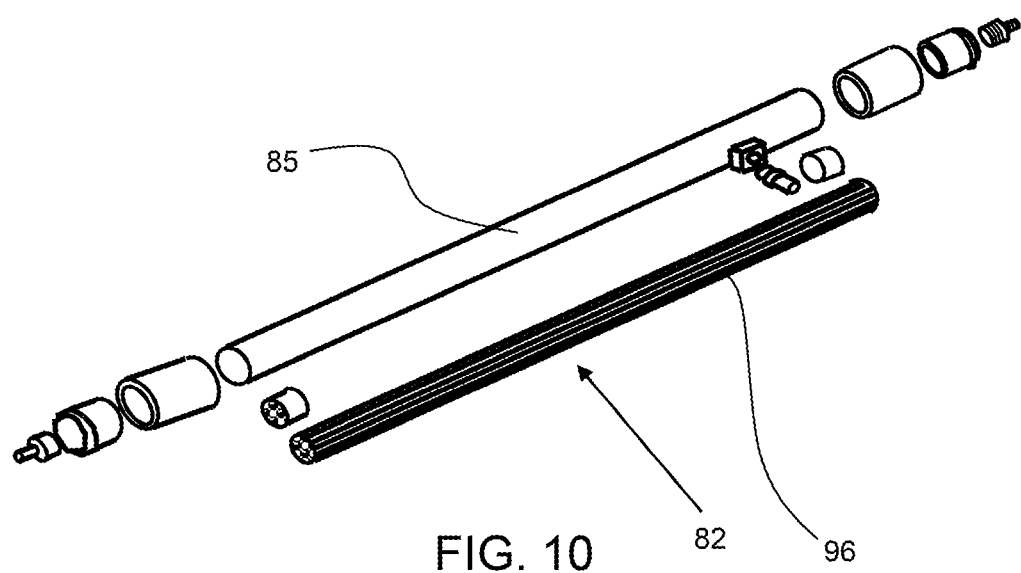
FIGS. 10 is an exploded view of an exemplary shell and tube assembly.

In FIG. 10, an exploded view of the module 82 showing all its constituent components is shown. The ion conducting tubes 96, or ionomer tubes are shown outside of the module enclosure 85.

Figure 11:
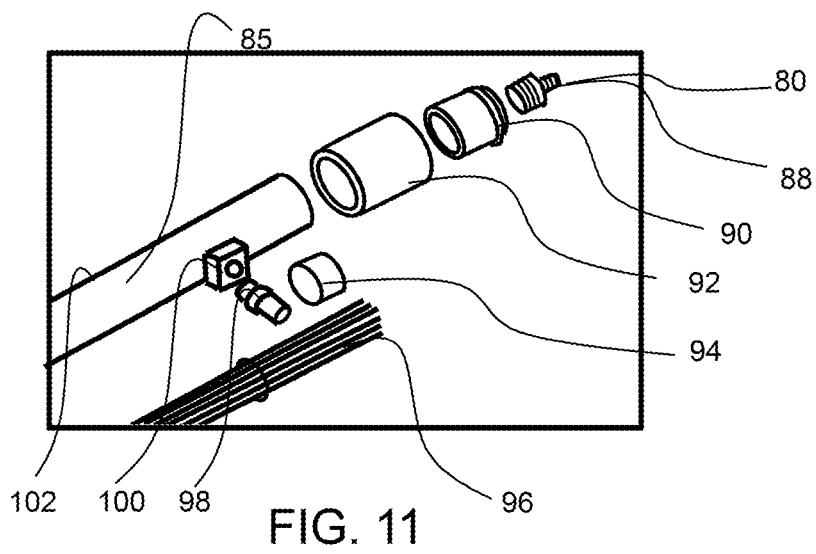
FIGS. 11 is an exploded view of and inlet end of an exemplary shell and tube assembly.

In FIG. 11, a section of the module is shown. Liquid flows through ed flow fitting 88, the fitting 88 connects to the bushing 90. An adapter 92 connects the bushing to the shell. This forms the inlet 80. The shell 102, or module enclosure 85, may be a tube, such as a PVC pipe, which is used to house the plurality of ionic tubes. The plurality of ionic tubes 96 are held together with a slug of cured potting resin 94. The cured potting resin 94 may also bonds the plurality of ionic tubes 96 to the shell 102. A machined part 100 is solvent welded to the shell 102 by using solvent cement. The vacuum fitting 98 is then screwed into the part to complete the assembly.

Figure 12:
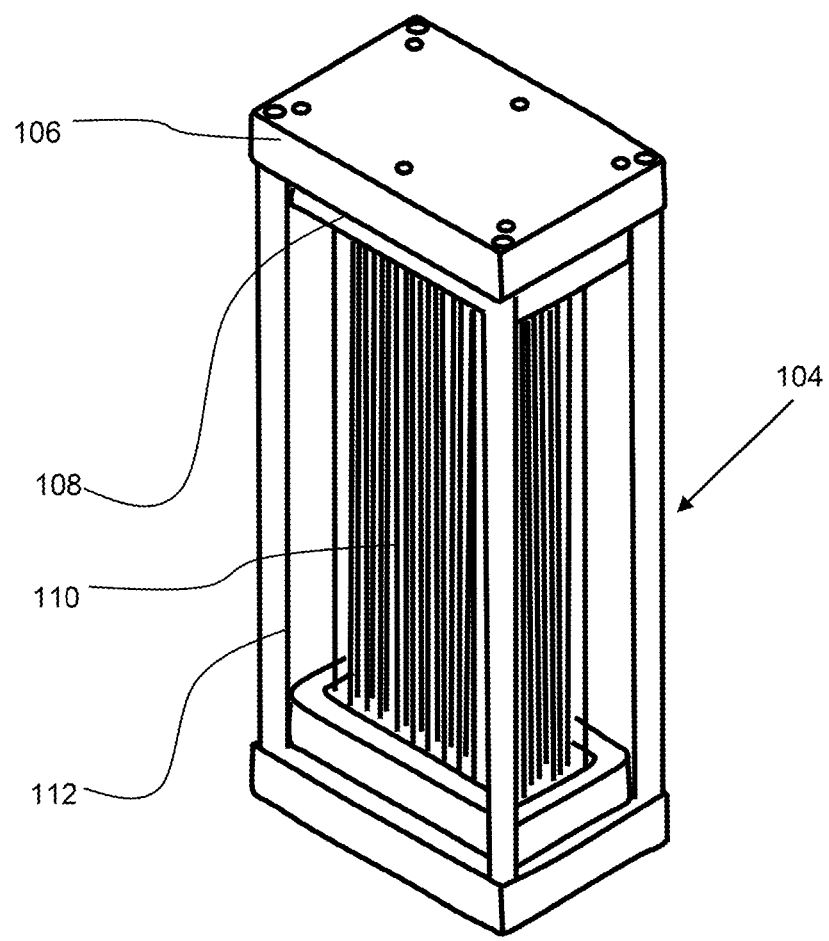
FIG. 12 is a perspective view of a liquid desiccant model.
Figure 13:
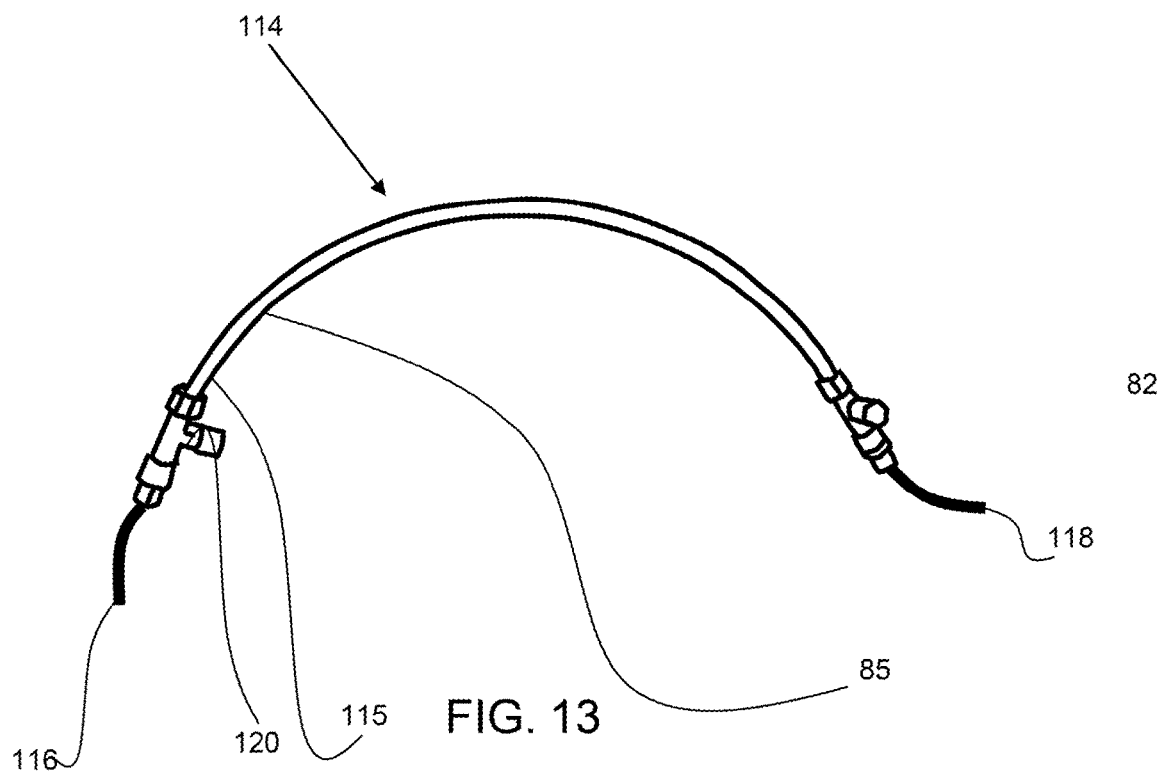
FIG. 13 is a top down view of an exemplary medical gas dehumidifier.

In FIG. 12, a module used for liquid desiccant dehumidification 104 is shown. The module consists of a header 106, a tube sheet 108 specifically designed for minimizing leakages. The ion conducting tubes 110 are potted with the tube sheet. Structural columns 112 are used to provide support to prevent the module from buckling. A module as generally shown in FIG. 12 might be an Evaporative Cooling module. In an HVAC system, heat is generated by the sun shining on the building, the computers, and people. The heat is picked up in the air handlers which are indirectly tied to the refrigerant through several heat exchangers. The heat boils the refrigerant from a liquid to a vapor. In order to convert this vapor back to a liquid, we use cooling tower water. The refrigerant vapor is condensed, and heat is transferred to the water with the help of a heat exchanger. The purpose of the cooling towers is to cool the warm water returning from the heat exchanger. The cooling towers consist of a plurality of ionic membrane tubes through which the warm water flows. Some of the warm water vaporizes, and the vapor transfers through the ionic membranes. A fan providing a draft drives the water vapor away from the cooling tower. This process cools the warm water down by removal of latent heat of vaporization. The cooled water is then looped back to the heat exchanger to condense the refrigerant vapor. FIG. 9 shows a model evaporative cooling membrane module. These membrane modules provide an advantage over conventional cooling towers as they provide closed circuit evaporative cooling. This prevents microbial growth which is common to open circuit systems and hence a much more As shown in FIG. 13, an ion conducting tube 115 that extends from a tube inlet 116 to a tube outlet 118 is used to dry gases for medical and analytical applications. The tube is contained inside a shell 115, module enclosure 85, which is terminated with the help of tee fittings 120. This device is operated in two modes. In mode one, the gases which need to be dried flow through the tube and are dried with the help of a vacuum or purge gas on the shell side. In mode two, the gases which need to be dried flow through the shell and are dried with the help of purge gases flowing through the tube.

Medical gas conditioning: Water vapor needs to be removed from breath samples for accurate breath gas analysis. The most common source of problems in breath gas analysis is the water vapor present in the sample. It can cause condensation in gas sampling lines and measurement cells as well as interference with (IR) $CO_2$ monitoring. The humidity exchangers shown in FIG. 9 selectively remove only water vapor from the sample, virtually eliminating this source of analyzer failure. The gas flows through the ionic membrane tube and is dried out by using purge gas or applying vacuum on the shell side or vice-versa. Humidity Exchangers are widely used for Anesthesia monitoring, Stress testing/Pulmonary function testing, Capnography (CO2 monitoring) and Asthma monitoring (Nitric Oxide).

Figure 14:
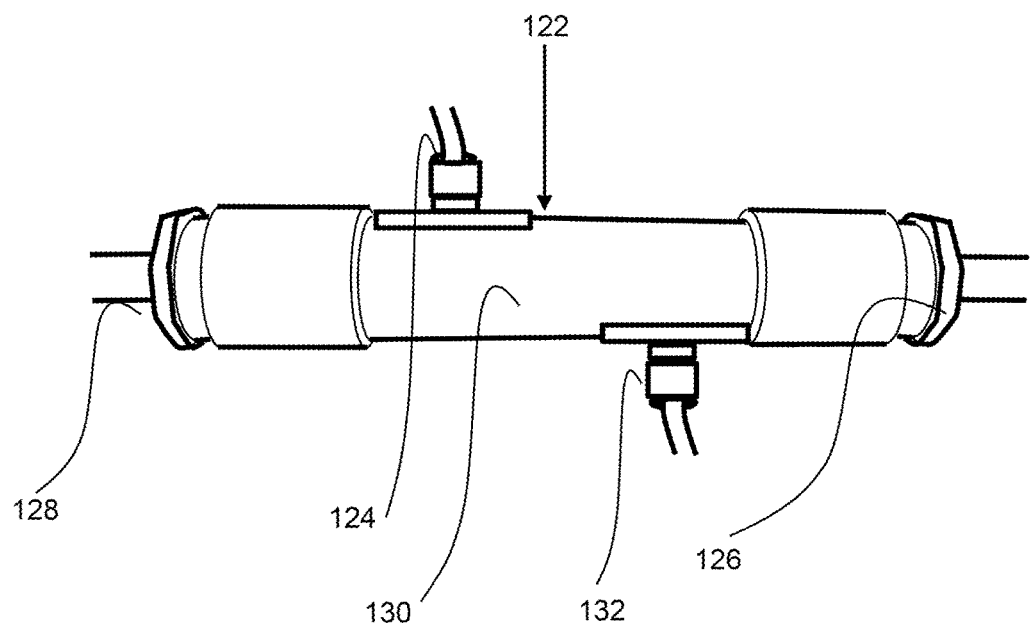
FIG. 14 is a side view of an exemplary fuel cell gas dehumidifier.

As shown in FIG. 14, a plurality of ionic tubes 130 is used to dry or humidify fuel cell gases. The device 122 can be operated in two modes. Fuel cell gases which need to be humidified flow into the plurality of ionic tubes through the inlet 126 and through the outlet 128. Fuel cell gases that need to be purged of moisture flow into the shell through the inlet 124 and out through the outlet 132. In the second mode, fuel cell gases that need to be dried flow into the plurality of ionic tubes through the inlet 126 and through the outlet 128. Fuel cell gases that need to be humidified flow into the shell through the inlet 124 and out through the outlet 132.

Fuel cell humidifiers: Hydrogen flowing into the fuel cell needs to be humidified in order to achieve optimum performance of fuel cell. Gas humidifiers shown in FIG. 14 are tube-in-shell humidity exchangers that transfer heat and water vapor between two gas streams. They may operate as either water-to-gas or gas-to-gas humidity exchangers. Water-to-gas humidifiers have liquid water on one side of the tube wall and a dry gas on the other. This arrangement offers the greatest amount of humidification; however, the reaction of the water molecules moving through the tubing wall absorbs heat. To counter this cooling effect, the inlet water must be heated. Hot, circulated deionized water should be used to optimize performance. Gas-to-gas humidifiers use counter-flowing wet and dry gas streams to move heat and humidity from one stream to the other. These units are energy efficient, as they do not require any additional power or heat. When gas passes inside the ionic tubing, water is absorbed by and moves through the walls of the tubing. The movement of water is driven by the humidity gradient between the inside and outside of the tubing. Since only water molecules move through the tubing walls, liquid water is prevented from becoming entrained in the gas stream.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents

What is claimed is:

1. An ion conducting polymer module system comprising:
   a) a plurality of ion conducting tubes each comprising:
      i) a composite ion conducting sheet comprising:
         a permeable support material; and
         an ion conducting polymer that is imbibed into the permeable support material and extending along a surface of the permeable support material as a surface layer;
         an overlap area formed by an outer layer of the composite ion conducting sheet over an inner layer of the composite ion conducting sheet;
         wherein the overlap area is a bonded area consisting of the surface layer of ion conducting polymer of the outer layer of the composite ion conducting sheet being bonded directly to the surface layer of ion conducting polymer of the inner layer of the composite ion conducting sheet to form said ion conducting tube;
         wherein only the ion conducting polymer forms said bonded area between the outer layer and the inner layer;
         wherein the tube has a tube surface area that is the product of an outer circumference of the tube and a length of the tube, and wherein the overlap area is no more than 30% of the tube surface area;
      ii) a length from an inlet end to an outlet end; and
      iii) a tube conduit extending along said length,
   b) a module having a module inlet and a module outlet;
   c) a feed fluid that flows through the module inlet, through the tube conduit of the plurality of ion conducting tubes and out the module outlet;
   d) a process fluid that flows around the ion conducting tube;
   wherein moisture is exchanged between the feed fluid and the process fluid and wherein moisture passes through the ion conducting tube.

2. The ion conducting polymer module system of claim 1, wherein the module comprises a module enclosure that extends around the ion conducting tube and contains said process fluid around the ion conducting tube.

3. The ion conducting polymer module system of claim 1, wherein moisture passes from the process fluid to the feed fluid in the ion conducting tube to reduce a moisture concentration of the process fluid.

4. The ion conducting polymer module system of claim 1, wherein process fluid is a breath sample flow of gas.

5. The ion conducting polymer module system of claim 1, wherein the process fluid is an analytical gas.

6. The ion conducting polymer module system of claim 1, wherein feed fluid is a breath sample flow of gas.

7. The ion conducting polymer module system of claim 1, wherein the feed fluid is an analytical gas.

8. The ion conducting polymer module system of claim 1, wherein moisture passes from the feed fluid to the process fluid in the ion conducting tube to reduce a moisture concentration of the process fluid.

9. The ion conducting polymer module system of claim 1, wherein the process fluid is a liquid and wherein water passes from the process fluid to the feed fluid to increase the moisture in the feed fluid.

10. The ion conducting polymer module system of claim 2, further comprising a tube sheet coupled with at least one of the module inlet or the module outlet and wherein the plurality of ion conducting tubes are potted with the tube sheet.

11. The ion conducting polymer module system of claim 9, wherein the process fluid is water having a saline concentration wherein the ion conducting polymer module system is part of a desalination process.

12. The ion conducting polymer module system of claim 1, wherein the thickness of the composite ion conducting sheet is no more than 25 microns.

13. The ion conducting polymer module system of claim 1, wherein the module has a vacuum port and wherein a vacuum is drawn within the module.

14. The ion conducting polymer module system of 1, wherein the ion conducting tube is a longitudinally wrapped tube, wherein the overlap area extends longitudinally along the length of the tube.

15. The ion conducting polymer module system of 1, wherein the ion conducting tube is a spirally wrapped tube having a wrap angle of the composite ion conducting sheet around the ion conducting tube.

16. The ion conducting polymer module system of 1, wherein the tube has a tube surface area that is the product of an outer circumference of the tube and a length of the tube, and wherein the overlap area is no more than 20% of a tube surface area.

17. The ion conducting polymer module system of 1, wherein the ion conducting polymer is a cation conducting polymer.

18. The ion conducting polymer module system of 1, wherein the ion conducting polymer is an anion conducting polymer.

19. The ion conducting polymer module system of 1, wherein the support material is a porous fluoropolymer having pores.

20. The ion conducting polymer module system of 19, wherein the porous fluoropolymer is expanded polytetrafluoroethylene.

* * * * *